US007491388B1

(12) United States Patent
Mc Intosh et al.

(10) Patent No.: US 7,491,388 B1
(45) Date of Patent: Feb. 17, 2009

(54) USES OF FIBROBLASTS OR SUPERNATANTS FROM FIBROBLASTS FOR THE SUPPRESSION OF IMMUNE RESPONSES IN TRANSPLANTATION

(75) Inventors: Kevin R. Mc Intosh, Ellicott City, MD (US); Joseph D. Mosca, Ellicott City, MD (US); Elena N. Klyushnenkova, Baltimore, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 1080 days.

(21) Appl. No.: 09/807,810

(22) PCT Filed: Nov. 4, 1999

(86) PCT No.: PCT/US99/25963

§ 371 (c)(1),
(2), (4) Date: Jul. 10, 2001

(87) PCT Pub. No.: WO00/29001

PCT Pub. Date: May 25, 2000

Related U.S. Application Data

(60) Provisional application No. 60/108,234, filed on Nov. 13, 1998.

(51) Int. Cl.
*A01N 65/00* (2006.01)
*A61K 45/00* (2006.01)

(52) U.S. Cl. .................................. 424/93.7; 424/278.1

(58) Field of Classification Search .............. 424/278.1, 424/93.7, 520, 537; 435/384
See application file for complete search history.

(56) References Cited

U.S. PATENT DOCUMENTS 5,733,542 A 3/1998 Haynesworth et al.
5,736,396 A * 4/1998 Bruder et al.

FOREIGN PATENT DOCUMENTS

WO WO96/40178 12/1996
WO WO96/40887 12/1996

OTHER PUBLICATIONS

Soiffer, R.J., et al. Blood, Apr. 15, 1997; 89(8):3039-3047.*
Bosi. A., et al. Leukemia. 1997; 11:420-424.*
Bowlin, et al., *J. Interferon Res.*, vol. 3, No. 1, pp. 19-31 (1983), Abstract Only.
Posavad, et al., *J. Virol.*, vol. 66, No. 11, pp. 6264-6272 (Nov. 1992), Abstract Only.
Shimabukuro, et al., *Immunology*, vol. 76, pp. 344-347 (1992).
Donnelly, et al., *Exp Eye Res.*, vol. 56, pp. 157-165 (1993), Odd Pages Only, 157, 159, 161, 163 165.

* cited by examiner

*Primary Examiner*—G. R Ewoldt
(74) *Attorney, Agent, or Firm*—McAndrews, Held & Malloy, Ltd.

(57) ABSTRACT

Disclosed is a method of inducing a reduced immune response to a transplant in a recipient by treating said recipient with an amount of fibroblasts or a supernatant from a fibroblast culture effective to reduce or inhibit host rejection of the transplant. The fibroblasts or a supernatant from a fibroblast culture can be administered before, at the same time as, or after the transplant. This method is effective in reducing an immune response to a transplant without compromising the immune response to other foreign antigens. Also disclosed is a method of inducing a reduced immune response against a host by foreign tissue, i.e., graft versus host disease.

2 Claims, 3 Drawing Sheets

USES OF FIBROBLASTS OR SUPERNATANTS FROM FIBROBLASTS FOR THE SUPPRESSION OF IMMUNE RESPONSES IN TRANSPLANTATION

The application claims priority based on provisional application Ser. No. 60/108,234, filed Nov. 13, 1998.

The present invention relates to the field of preventing or treating host rejection of a transplant and/or graft versus host reaction.

BACKGROUND OF THE INVENTION

Tolerance is the acquired lack of responsiveness to an antigen to which an immune response would normally occur. Typically, to induce tolerance, there must be an exposure to a tolerizing antigen, which results in the death or functional inactivation of certain lymphocytes. Complete tolerance is characterized by the lack of a detectable immune response, either antibody or cell mediated, to the second antigenic challenge. Partial tolerance is typified by the quantitative reduction of an immune response.

The function of the immune system is to eliminate foreign bodies which may contain pathogens, and to maintain unresponsiveness or tolerance against self antigen. T cell tolerance is achieved 1) in the thymus where thymocytes reactive for self-peptides are eliminated by clonal deletion (central tolerance), and 2) in the periphery by exposure to self-antigens under tolerogenic conditions (peripheral tolerance).

Unfortunately, the immune system does not distinguish beneficial intruders, such as transplanted tissue, from those that are harmful, and thus the immune system rejects transplanted tissue or organs. Rejection of transplanted organs is significantly mediated by alloreactive T cells present in the host which recognize donor alloantigens or xenoantigens.

At present, patients rejecting transplants are treated with powerful immunosuppressive drugs. The infusion of individuals with drugs that prevent or suppress T-cell immune response does inhibit transplant rejection, but can also result in general immune suppression, toxicity and even death due to opportunistic infections. Because of the toxicity and incomplete response rate to conventional treatment of donor tissue rejection, alternative approaches are needed to treat patients who cannot withstand or do not respond to current modes of drug therapy.

Accordingly, there is a need for the reduction or elimination of an unwanted immune response by a host to a transplant as a method to avert host rejection of donor tissue. Also advantageous would be a method to eliminate or reduce an unwanted immune response by a donor tissue against a recipient tissue, known as graft-versus-host disease.

It has been reported that human gingival fibroblasts, when both treated with IFN-γ and contacted with T cells, are ineffective stimulators of alloreactive peripheral T cells and inhibited a proliferative response of allogeneic antigen presenting cells or mitogen stimulated cells. (Shimabukuro, Y. et al., *Immunology* 76:344-347 (1992)).

SUMMARY OF THE INVENTION

It has been discovered that human fibroblasts can be used in transplantation to ameliorate a response by the immune system such that an immune response to an antigen(s) will be reduced or eliminated. The reduction or elimination by fibroblasts (FBLs) of an immune response as described herein can be used as a method to ameliorate an immune response in a recipient against donor tissue or organ transplant. Thus, in one aspect, the method of the present invention is particularly useful for suppressing an unwanted T cell immune response to donor tissue transplant.

Accordingly, in one aspect, the method of the present invention provides contacting the recipient of donor tissue with isolated fibroblasts. In one embodiment of this aspect, the method involves administering isolated fibroblasts to the recipient of donor tissue. The fibroblasts can be administered to the recipient before, at the same time as, or after the transplant. The fibroblasts can be either autologous or allogeneic to the recipient. The allogeneic fibroblasts can be obtained from the donor and therefore are autologous to the transplanted tissue. In another aspect of the invention, the allogeneic fibroblasts can also be obtained from a source other than the donor and such source need not be matched either to the donor type or the recipient type.

The fibroblasts can also be administered to the recipient as part of the transplant. To this objective, the present invention provides a method for reducing or ameliorating an immune response by providing to the recipient donor tissue or organ that is perfused with or includes fibroblasts. In a preferred embodiment, the fibroblasts are allogeneic to the recipient, preferably allogeneic to both donor and recipient. The fibroblasts ameliorate an immune response by the recipient's T cells against the foreign tissue when it is transplanted into the recipient.

In another embodiment, the donor tissue or organ is perfused with or includes fibroblasts obtained from a source other than the donor which need not be matched either to the donor or recipient MHC type.

In another aspect, the method of the present invention provides treating a patient who has received a transplant, in order to reduce the severity of or eliminate a rejection episode against the transplant, by administering fibroblasts to the recipient of donor tissue after the donor tissue has been transplanted into the recipient. The fibroblasts can be obtained from the recipient or donor, and preferably are obtained from a third party source.

The presentation of fibroblasts to a recipient undergoing an adverse immune response to a transplant reduces or induces hyporesponsiveness of T cells to further antigenic stimulation thereby reducing or eliminating an adverse response by activated T cells to donor tissue.

In a further aspect of the present invention, there is provided a method of reducing an immune response by donor tissue against a recipient, i.e. graft versus host response, comprising treating the donor tissue or organ with fibroblasts ex vivo prior to transplantation of the tissue or organ into the recipient. The fibroblasts may be autologous or allogeneic to the recipient. The allogeneic fibroblasts may be obtained from the donor, or preferably the fibroblasts are allogeneic to both donor and recipient. The fibroblasts reduce the responsiveness of T cells in the transplanted tissue that may be activated against recipient cells such that the tissue may be introduced into the recipient's (host's) body without the occurrence of, or with a reduction in, an adverse response of the donor tissue to the host. Thus, what is known as "graft versus host" disease may be averted.

In a still further embodiment, the donor tissue or organ may be first exposed to recipient tissue ex vivo, to "preactivate" the T cells in the donor tissue. The donor tissue is then contacted with fibroblasts, preferably third party fibroblasts. The fibroblasts will reduce or inhibit an adverse secondary immune response by T cells in the donor tissue against antigenic stimulation by the recipient when the donor tissue is placed into the recipient.

A further embodiment of the present invention includes administering third party fibroblasts to the recipient after transplantation to reduce or prevent the adverse immune response of the recipient against donor tissue.

In another embodiment, the fibroblasts may be administered to the graft recipient intravenously prior to, during or after the transplant.

Thus, in accordance with preferred embodiments of the present invention, human fibroblasts are employed to treat transplant rejection and or graft versus host disease as a result of a transplant and or to prevent or reduce transplant rejection and or graft versus host disease. Fibroblasts, human or non-human, may also be employed to facilitate the use of xenogeneic grafts or transplants.

It further has been discovered that the supernatant derived from fibroblast cultures and fibroblast/mixed lymphocyte reaction cultures has a suppressive effect on a T cell response to an alloantigen. Thus, the present invention further provides a method of use of supernatants.

DETAILED DESCRIPTION OF THE INVENTION

Figure 2:
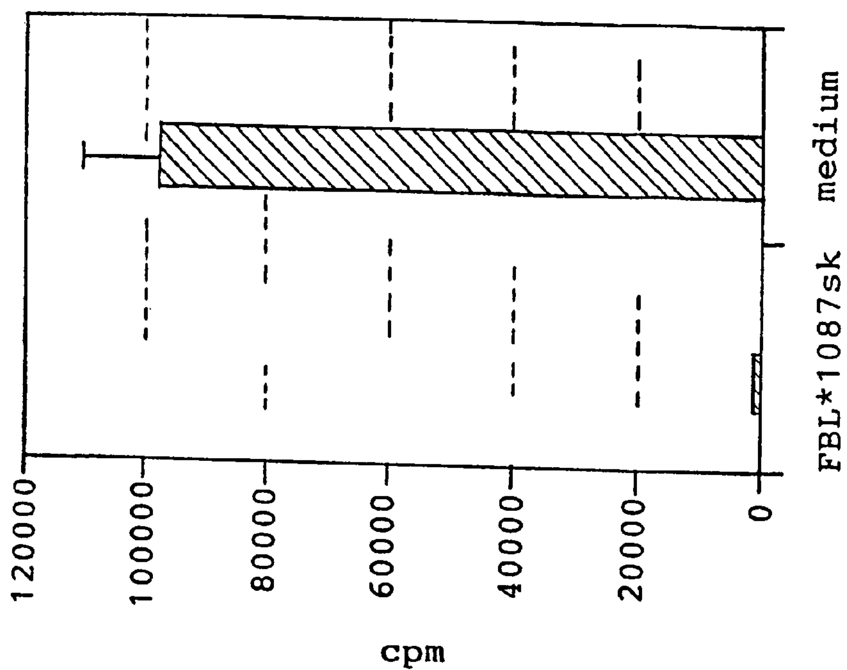
FIG. 2. Human fibroblasts suppressed an ongoing mixed lymphocyte reaction (MLR) between lymphocytes from two different individuals. The fibroblasts were mismatched to both the stimulator and responder cells in the MLR. The stimulated T cells were incubated with freshly trypsinized fibroblasts.

As defined herein, an allogeneic fibroblast is obtained from a different individual of the same species as the recipient. Donor antigen refers to antigens expressed by the donor tissue to be transplanted into the recipient. Alloantigens are antigens which differ from antigens expressed by the recipient. Donor tissue to be transplanted is the transplant.

The inventors have discovered that when human fibroblasts are contacted with allogeneic T lymphocytes, in vitro, fibroblasts suppressed an ongoing mixed lymphocyte reaction. Normally, co-culturing cells from different individuals results in a T cell response, manifested by activation and proliferation of the T cells, known as a mixed lymphocyte reaction (MLR). Contacting T cells undergoing an MLR with fibroblasts suppressed the MLR.

In one aspect, the present invention provides a method to reduce or inhibit or eliminate an immune response to donor tissue or organ transplant in a recipient thereof. In one aspect of the invention, the method involves administering fibroblasts to the recipient. The fibroblasts are employed in an amount effective to ameliorate, inhibit or reduce the recipient's T cell response to donor tissue or organ.

Accordingly, the present invention provides a method of reducing, inhibiting or eliminating an immune response by administering fibroblasts to a recipient of a donor tissue or organ. The fibroblasts are preferably third party fibroblasts. In one embodiment, the fibroblasts are administered to the recipient contemporaneously with the transplant. Alternatively, the human fibroblasts can be administered prior to the administration of the transplant. For example, the human fibroblasts can be administered to the recipient about 3 to 7 days before transplantation of the donor tissue. As a further alternative, the fibroblasts can be administered after the transplant.

Thus, fibroblasts can be used to condition a recipient's immune system to donor or foreign tissue by administering to the recipient, prior to, or at the same time as transplantation of the donor tissue, fibroblasts in an amount effective to reduce or eliminate an immune response by the recipient's T cells. The fibroblasts affect the T cells of the recipient such that the T cells are hyporesponsive and the T cell response is reduced or eliminated when the recipient is presented with donor or foreign tissue. Thus, host rejection of the transplant may be avoided or the severity thereof reduced.

The inventors have further discovered that when T lymphocytes that have already been exposed to antigenic stimulation, i.e. are activated, are subsequently exposed to fibroblasts, the T cells do not produce an immune response to subsequent antigenic stimulation. Thus, fibroblasts induce a state of hyporesponsiveness to the antigen that stimulated the T cells, or to stimulation from other antigens.

These unexpected results demonstrated that activated T cells, after exposure to allogeneic human fibroblasts, were made hyporesponsive to further antigenic stimulation, thereby reducing or ameliorating an ongoing adverse immune response.

Accordingly, the present invention provides a method for treating a patient who is undergoing an adverse immune response to a transplant by administering fibroblasts to such patient. In a preferred embodiment, the fibroblasts are obtained from a third party that need not be MHC matched to either the donor or the recipient.

The fibroblasts are administered to the recipient in an amount effective to reduce or eliminate the immune response, thereby ameliorating the adverse immune response.

In another aspect, the present invention provides a method to reduce or inhibit or eliminate an immune response by donor tissue or organ transplant against a recipient thereof (graft versus host). Accordingly, the invention provides contacting a donor organ or tissue with fibroblasts prior to transplant, preferably with pre-stimulation of T cells in the donor tissue with recipient tissue. The fibroblasts ameliorate, inhibit or reduce an adverse response by the donor tissue against the recipient.

In another embodiment, the fibroblasts may be administered to the graft recipient intravenously prior to, during or after the transplant.

Fibroblasts can thus be used to precondition donor or foreign tissue to a recipient's immune system. In one embodiment, this can be done by contacting the donor or foreign tissue ex vivo with isolated fibroblasts, prior to transplant of the tissue into the recipient. In this embodiment, donor tissue or organ can be co-incubated with recipient fibroblasts for from less than 1 day co-incubation to about 7 days prior to placement of the tissue into the recipient. The fibroblasts are believed to suppress T cells present on or in the tissue or organ, thus making the T cells in the tissue hyporesponsive to the recipient when it is subsequently placed into the recipient. Thus, treatment of the tissue or organ with fibroblasts ameliorates the incidence and/or severity of graft versus host disease, wherein activated T cells present in the transplanted tissue attack the host. In a preferred embodiment, the fibroblasts are allogeneic to both donor and recipient.

Thus, in the context of bone marrow (hematopoietic stem cell) transplantation, attack of the host by the graft can be reduced or eliminated. Donor marrow can be pretreated with isolated fibroblasts prior to implant of the bone marrow or peripheral blood stem cells into the recipient. The fibroblasts inhibit or reduce the T cell response such as to reduce or eliminate a recipient from being adversely affected by the donor tissue, i.e. the therapy reduces or eliminates graft versus host response.

In a further embodiment, a transplant recipient suffering from graft versus host disease may be treated to reduce or eliminate the severity thereof by administering to such recipient isolated fibroblasts, which can be autologous to either the recipient or donor, or can be third party fibroblasts, in an amount effective to reduce or eliminate a graft rejection of the host. The fibroblasts inhibit the activated T cells in the donor tissue from mounting an immune response against the recipient, thereby reducing or eliminating a graft versus host response.

The recipient's fibroblasts may be obtained from the recipient prior to the transplantation and may be stored and/or culture-expanded to provide a reserve of fibroblasts in sufficient amounts for providing multiple treatments, for example, in an ongoing graft attack against host.

In yet another method of the present invention, the donor tissue is exposed to isolated fibroblasts such that the fibroblasts integrate into the organ graft itself prior to transplantation. In this situation, any alloreactive host cells that escaped standard treatment to prevent transplant rejection, e.g., drug-mediated immunosuppression, would be immunologically suppressed by the fibroblasts as they entered the graft to destroy it. The fibroblasts may be autologous or allogeneic to the recipient and preferably are obtained from a party other than the donor or recipient.

In accordance with the methods of the present invention described herein, it is contemplated that the fibroblasts of the present invention can be used in conjunction with current modes of treating donor tissue rejection or graft versus host disease. An advantage of such use is that by ameliorating the severity of the immune response in a transplant recipient, the amount of drug used in treatment and/or the frequency of administration of drug therapy can be reduced, resulting in alleviation of general immune suppression and unwanted side effects.

It is further contemplated that only a single treatment with the fibroblasts of the present invention may be required, eliminating the need for chronic immunosuppressive drug therapy. Alternatively, multiple administrations of fibroblasts may be employed.

Accordingly, the invention described herein provides for preventing or treating transplant rejection by administering the fibroblasts in a prophylactic or therapeutically effective amount for the prevention or treatment or amelioration of transplant rejection of an organ or tissue from the same species, or a xenograft organ or tissue transplant and or graft versus host disease.

Administration of a single dose of fibroblasts may be effective to reduce or eliminate the T cell response to tissue allogeneic to the T cells or to "non-self" tissue, particularly in the case where the T lymphocytes retain their nonresponsive character (i.e., tolerance or anergy) to allogeneic cells after being separated from the fibroblasts.

The dosage of the active ingredient varies within wide limits and will, of course be fitted to the individual requirements in each particular case. In general, in the case of parenteral administration, it is customary to administer from about 0.01 to about 20 million cells per kilogram of recipient body weight. The number of cells used will depend on the weight and condition of the recipient, the number of or frequency of administrations and other variables known to those of skill in the art. The cells can be administered by a route which is suitable for the tissue or organ to be transplanted, they can be administered systemically, i.e., parenterally, by intravenous injection or can be targeted to a particular tissue or organ, such as bone marrow. The human fibroblasts can be administered via a subcutaneous implantation of cells or by injection of stem cells into connective tissue, for example muscle.

The cells can be suspended in an appropriate diluent, at a concentration of from about 0.01 to about $5\times10^6$ cells/ml. Suitable excipients for injection solutions are those that are biologically and physiologically compatible with the cells and with the recipient, such as buffered saline solution or other suitable excipients. The composition for administration must be formulated, produced and stored according to standard methods complying with proper sterility and stability.

Although the invention is not limited thereof, fibroblasts can be obtained from skin for use in the methods described herein.

The inventors also discovered that the supernatants derived from fibroblast cultures can suppress an MLR between allogeneic cells. As used herein, supernatants derived from fibroblast cultures, also referred to herein as "fibroblast supernatant," can be obtained from fibroblasts cultured alone or fibroblasts co-cultured with cells undergoing an immune response, i.e., T cells undergoing a mixed lymphocyte reaction.

Fibroblast supernatants actively reduce the allogeneic T cell response in mixed lymphocyte reactions in a dose dependent manner. As with fibroblasts, supernatants from fibroblast cultures from different donors do not exhibit specificity of reduced response with regard to MHC type.

In addition, the supernatants derived from mixed lymphocyte reactions contacted with fibroblasts also can suppress an MLR between allogeneic cells. These MLR/fibroblast supernatants actively reduce the allogeneic T cell response in mixed lymphocyte reactions in a dose dependent manner and do not exhibit specificity of reduced response with regard to MHC type.

It should be understood that the methods described herein may be carried out in a number of ways and with various modifications and permutations thereof that are well known in the art. It may also be appreciated that any theories set forth as to modes of action or interactions between cell types should not be construed as limiting this invention in any manner, but are presented such that the methods of the invention can be more fully understood.

The following examples further illustrate aspects of the present invention. However, they are in no way a limitation of the teachings or disclosure of the present invention as set forth herein.

EXAMPLE 1

Suppression of Mixed Lymphocyte Reaction

The mixed lymphocyte reaction measures the compatibility of the donor's surface antigens and is an indication of the likelihood of rejection of donor tissue. Cell surface antigens responsible for eliciting transplant rejection are class I and class II MHC antigens. T cells are alloreactive to foreign MHC antigens. Class I and II MHC molecules stimulate the mixed lymphocyte reaction.

To determine whether fibroblasts actively suppressed the allogeneic response, mixed lymphocyte reactions (MLR) were set up in tissue culture plates, with or without fibroblasts obtained from a donor unrelated to either the stimulator or responder cells.

Lymphocyte Preparation

Peripheral blood mononuclear cells (PBMC) were prepared by density gradient centrifugation on Ficoll-Paque (Pharmacia). Aliquots of cells were frozen in 90% FCS with 10% DMSO and stored in a liquid nitrogen. After thawing, the cells were washed twice with MSC medium (DMEM-low glucose and 10% FCS) and re-suspended in assay medium (ISCOVE'S with 25 mM Hepes, 1 mM sodium pyruvate, 100 μM non-essential amino acids, 100 U/ml penicillin, 100 μg/ml streptomycin, 0.25 μg/ml amphotericin B, $5.5\times10^{-5}$M 2-mercaptoethanol (all reagents from GibcoBLR) and 5% human AB serum (Sigma, MLR tested)).

To prepare the T cell-enriched fraction, PBMCs were depleted of monocytes and B cells by immunomagnetic negative selection. PBMCs were incubated with mouse anti-human CD19 and CD14 mAbs (no azide/low endotoxin (NA/LE) format) followed by biotin-conjugated goat anti-mouse IgG (multiple adsorption) Ab (all reagents from Pharmingen) and streptavidin microbeads (Miltenyi Biotec). Cells were then separated using a magnetic cell sorter (MACS, Miltenyi Biotec). The T cell-enriched fraction contained about 70-90% CD3+ cells.

Fibroblasts

Fibroblasts were human normal skin fibroblasts CCD-1087 Sk from 18 years old female obtained from ATCC (Cat# CRL-2104) and were maintained in DMEM-low glucose/10% FCS.

Activated T Cell/Fibroblast Cultures

Fibroblasts (third party) were plated at $1\times10^6$ cells per tissue culture dish 4 days prior to mixing with T cells. IFN-γ (Pharmingen, 5 ng/ml) was added for 3 days and intensively washed out prior to mixing the fibroblasts with T cells.

Primary (1°) MLR.

Responder cells and stimulator cells were obtained from unrelated individuals. PBMCs used for stimulation were X-ray irradiated with 3,000 rad using Cabinet X ray system (Faxitron X ray, Buffalo Grove, Ill.). Enriched T cells were used as responders.

Figure 1:
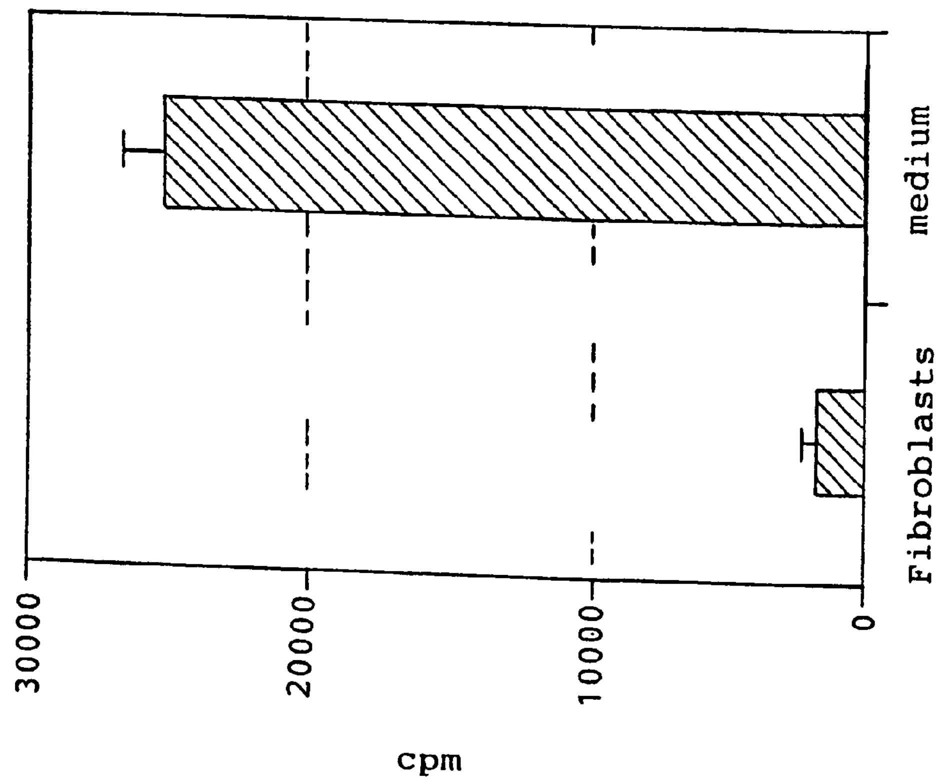
FIG. 1. Human fibroblasts suppressed an ongoing mixed lymphocyte reaction (MLR) between lymphocytes from two different individuals. The fibroblasts were mismatched to both the stimulator and responder cells in the MLR. The stimulated T cells were incubated with pre-plated fibroblasts.

A. T cells from donor 248 were stimulated by irradiated PBMCs from donor 244 for 7 days (37° C. in 5% $CO_2$), then collected and incubated with pre-plated FBLs for 24 hours. ($1\times10^5$ T cells/well, $2\times10^4$ FBLs per well). $^3$H-thymidine was added for an additional 18 hours of the culture period to measure T cell proliferation. The results shown in FIG. 1 indicate that fibroblasts suppressed an ongoing MLR.

B. T cells from donor 273 were mixed with irradiated PBMCs from donor 248 ($1.5\times10^5$ cells/well each) in 96-well plates. Freshly trypsinized fibroblasts were added 4 days later no IFN, $2\times10^4$ cells/well and cultures were incubated for an additional 3 days (7 days total for the MLR). $^3$H-thymidine was added for an additional 18 hours. The results shown in FIG. 2 indicate that fibroblasts also suppressed on ongoing MLR when not attached to the well surface.

EXAMPLE 2

Induction of T Cell Non-Responsiveness

T cells were activated in the 1° MLR (T248@244) were collected, washed once with MSC medium (DMEM-LG/10% FCS) and re-suspended in assay medium at $1\times10^6$ cells/ml. Cells were mixed with pre-plated fibroblasts at an approximate ratio of 10 T cells per fibroblast. T cells were incubated with fibroblasts for 3 days. In control cultures, T cells were incubated alone.

Restimulation Assay

Figure 3:
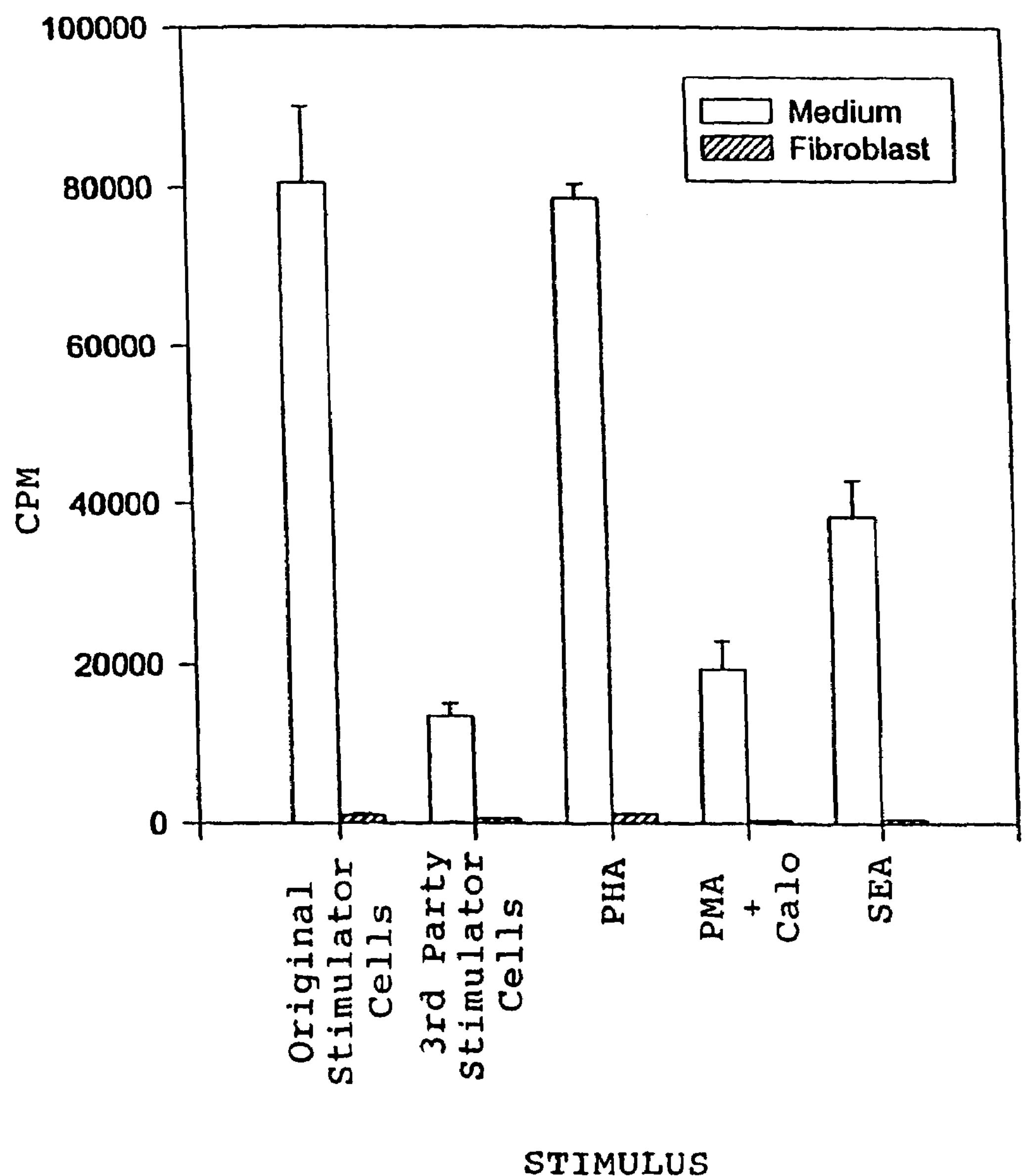
FIG. 3. Human fibroblasts suppressed a secondary mixed lymphocyte reaction. Restimulation of previously stimulated T cells, incubated with allogeneic fibroblasts, then contacted with allogeneic, autologous or third party stimulators, was suppressed.
Figure 4:
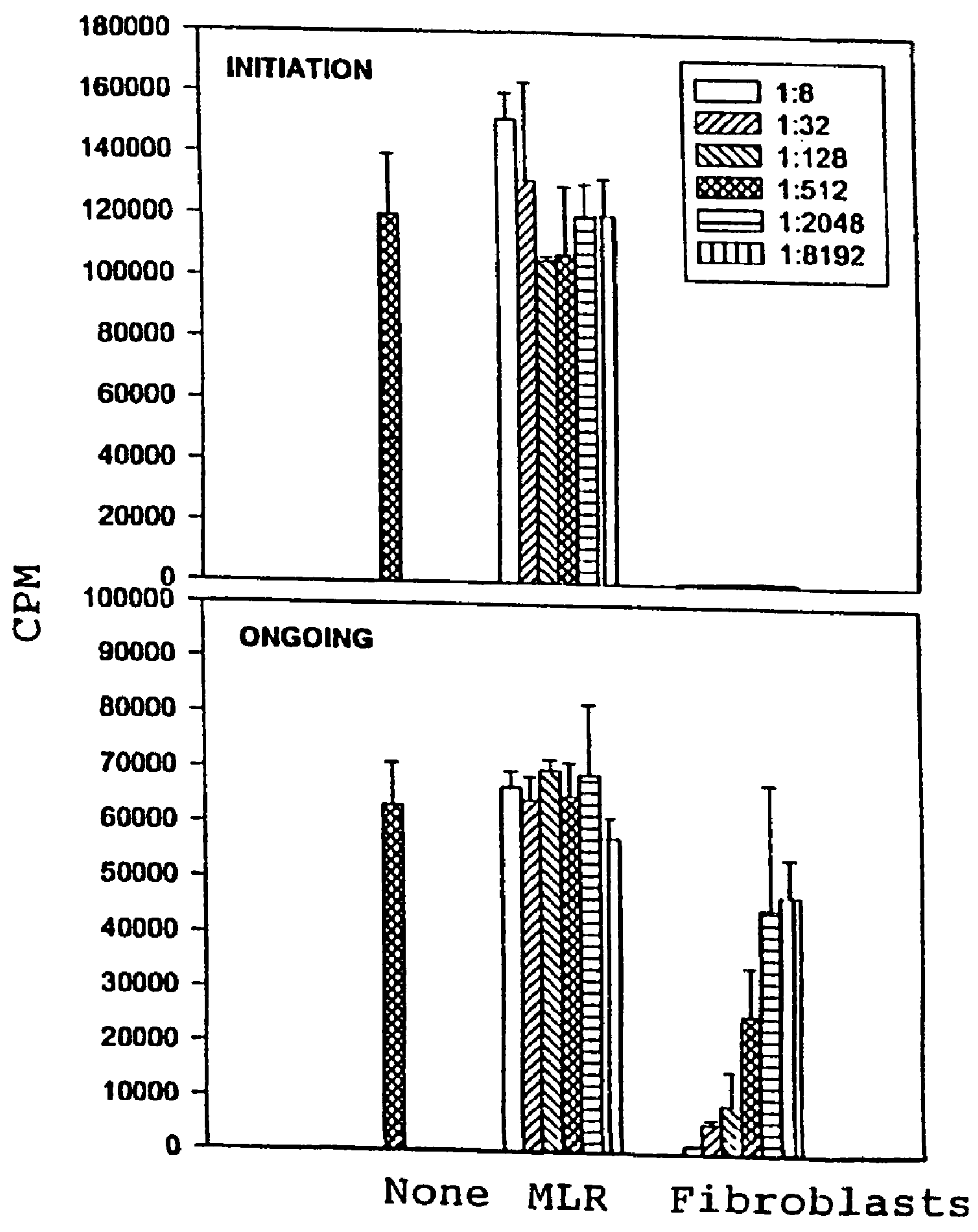
FIG. 4. Supernatant from fibroblast culture suppresses a mixed lymphocyte reaction.

The T cell cultures were collected, resuspended at $1\times10^6$ cells/ml, and added to 96-well plates ($5\times10^4$ cells/well in 50 microliters). They were mixed with various stimuli including original stimulator PBMCs from donor 244, third party stimulator cells, phytohemagglutinin (PHA, 5 micrograms/ml), phorbol myristate acetate plus calcium ionophore (PMA 10 nanogram/ml+CaIo Inanogram/ml), or staphylococcus enterotoxin A (SEA 100 nanograms/ml). Cells were pulsed overnight (18 hours) with $^3$H-thymidine (5 μCi/mmol, 1 μCi/well) on day 0, 1, 2, 3, 4, 5 or 6, then harvested. Results for day 2 are shown in FIG. 3. Previously stimulated T cells, subsequently exposed to allogeneic fibroblasts, were not re-stimulated in the presence of any of the stimuli.

EXAMPLE 3

Supernatant was collected from confluent cultures of adult dermal fibroblasts (#1087SK, from ATCC, Rockville, Md.). Cells were passage 6 and in culture for 1 month at the time of supernatant harvest. Conditioned media was harvested 3 days after media change. Supernatant ("Fibroblasts") was added at the indicated dilutions either at the initiation of MLR culture (top panel) or on day 4 of culture (ongoing, lower panel). The MLR consisted of responder T cells from donor 155 mixed with irradiated (3000R) stimulator PBMCs from donor 273. Both sets of cultures were pulsed with 3H-thymidine on day 6 of culture for 18 hrs. prior to harvesting the cells and determining the proliferative response assessed by thymidine incorporation into DNA. Controls consisted of MLR cultures to which nothing was added ("None") and cultures to which supernatant from an unrelated 3 day MLR culture was added ("MLR"). The results demonstrate that fibroblast supernatant totally suppressed the primary MLR when added at the initiation of culture. Suppression was powerful as shown by the inability to dilute out the effect, even at a 1:8192 dilution.

When added to ongoing cultures, the supernatant was more than 50% suppressive up to the 1:2048 dilution.

It is to be understood, however, that the scope of the present invention is not to be limited to the specific embodiments described above. The invention may be practiced other than as particularly described and still be within the scope of the accompanying claims.

What is claimed is:

1. A method of reducing an immune response against recipient tissue by donor tissue, comprising contacting the donor tissue with isolated fibroblasts in an amount effective to reduce an immune response by the donor tissue against the recipient;

wherein the fibroblasts are allogeneic both to the donor and to the recipient of the donor tissue.

2. A method of reducing an immune response against recipient tissue by donor tissue, comprising contacting the donor tissue with isolated fibroblasts in an amount effective to reduce an immune response by the donor tissue against the recipient;

wherein the donor tissue and the fibroblasts are contacted ex vivo prior to transplantation of the donor tissue; and wherein the donor tissue is exposed to recipient tissue prior to being contacted with the fibroblasts.

* * * * *